(12) United States Patent
Reitan (10) Patent No.: US 8,617,239 B2
(45) Date of Patent: Dec. 31, 2013

(54) CATHETER PUMP (75) Inventor: Oeyvind Reitan, Lund (SE)

(73) Assignee: Cardiobridge GmbH, Chingen (DE)

( * ) Notice: Subject to any disclaimer, the term of this patent is extended or adjusted under 35 U.S.C. 154(b) by 17 days.

(21) Appl. No.: 13/320,961

(22) PCT Filed: May 18, 2010

(86) PCT No.: PCT/EP2010/056772
§ 371 (c)(1),
(2), (4) Date: Nov. 17, 2011

(87) PCT Pub. No.: WO2010/133567
PCT Pub. Date: Nov. 25, 2010

(65) Prior Publication Data
US 2012/0059460 A1    Mar. 8, 2012

(30) Foreign Application Priority Data
May 18, 2009   (SE) ........................................ 0900637

(51) Int. Cl.
A61M 1/10 (2006.01)
(52) U.S. Cl.
USPC .............................. 623/3.12; 623/3.1; 600/16
(58) Field of Classification Search
USPC ........................................... 623/3.12; 600/16
See application file for complete search history.

(56) References Cited

U.S. PATENT DOCUMENTS 4,753,221 A    6/1988   Kensey et al.

FOREIGN PATENT DOCUMENTS

| DE | 10336902 | 8/2004 |
| EP | 0364293 | 4/1990 |
| WO | 9405347 | 3/1994 |

OTHER PUBLICATIONS

PCT/EP2010/056772 International Search Report dated Aug. 10, 2010 (4 pages).

*Primary Examiner* — Thomas J Sweet
*Assistant Examiner* — Matthew Schall
(74) *Attorney, Agent, or Firm* — Michael Best & Friedrich LLP (57) ABSTRACT The invention refers to a catheter pump to be positioned in the ascending aorta (11) near the aortic valve (10) of a human being, comprising an elongated sleeve 6 with a drive cable (5) extending through the sleeve and connectable at its proximal end to an external drive source and a drive rotor near the distal end of the drive cable (5) mounted on a drive shaft (4) being connected with the drive cable (5), wherein the drive rotor consist of a propeller (3) being enclosed in a cage (2) and wherein the propeller (3) and the cage (2) are foldable from an insertion position close to the drive shaft (4) to an expanded working position, characterized by means (7, 7a, 2a, 19) for anchoring the drive rotor (3) in the ascending aorta (11) near the aortic valve (10) after insertion. The invention also refers to a method to position the pumping means of a catheter pump in the ascending aorta (11) just above the aortic valve (10).

2 Claims, 8 Drawing Sheets

CATHETER PUMP

"The Reitan Catheter Pump System" is a temporary circulatory support system based on the concept of a foldable propeller at the tip of a flexible catheter. The system is used in patients with heart failure when the native heart is unable to support the body with sufficient oxygenated blood.

The system is described in European Patent EP 0768900 and in the Swedish patent applications 0801459-9 and 0801460-7 and in the following together with the latest improvements of the system. The contents of said publications are included as a part of the present application. The dimensions mentioned are preferred dimensions and not intended to restrict the protection claimed for the invention.

There are several blood pumps on the market, but most of them require major surgery to be implanted. The use of a foldable propeller has therefore the advantage that while folded during the insertion it makes it possible to introduce a large propeller with high-flow capacity into the body percutaneously and without a need of surgery. After deployment the pump has a large propeller during operation. The propeller is placed in a pump head at the distal end of the catheter. In addition to the propeller the pump head also consists of a cage made of filaments surrounding the propeller in order to protect the aorta against the propeller.

The insertion of the pump is accomplished via a puncture in the arterial system, preferably in the femoral artery in the groin through an introducer sheath. In an earlier version the pump is advanced into the high thoracic aorta with the pump head placed approximately 5 to 10 centimeters below the left subclavian artery. Once in position, the propeller and its protective cage are deployed via an umbrella-like mechanism at the proximal end of the flexible catheter. In this position the rotation of the propeller creates a pressure gradient inside the aorta. The blood pressure decrease created in the upper part of the aorta facilitates the ejection of the left ventricle. The increased pressure in the lower part of the aorta facilitates the perfusion of the internal organs, especially the kidneys.

The transmission of power to the propeller is accomplished via a rotating wire in the inner part of the catheter which is connected to a DC motor at the proximal end. The rotational speed of the DC motor can be adjusted and is monitored by a specially designed console.

"The CARDIOBRIDGE REITAN Catheter Pump System" consists of four main components: 1. the Catheter—pump head, 2. the drive unit, 3. the console, and 4. the purge set.

The REITAN Catheter Pump itself consists of a flexible outer and an inner catheter, which slide against one another to deploy the protective cage and unfold the propeller within the cage. There is a flexible drive wire running through the central lumen of the inner catheter. The inner catheter also has small channels to transport 20% glucose solution to the pump head for lubricating. One-third of the fluid is returned via the internal drive shaft lumen, ⅔rds of the fluid is delivered into the patient.

The Pump Head

The pump head mounted at the distal tip of the flexible catheter is 35 mm (10 French) during insertion whereas the deployed pump head measures approximately 19.5 mm. The rotation of the propeller transmitted via the rotating wire placed in the central lumen of the inner catheter starts at the proximal end of the catheter (the drive coupling), which via a magnetic field to a DC motor, is placed in a Drive Unit.

The Drive Unit

The drive unit contains the DC motor and is positioned at the bed side of the patient and has a magnetic coupling for connection to the catheter pump at one end (the drive coupling). The other end of the drive unit is connected to the console via an electric cable.

The Console

The primary functions of the console are to monitor and control the speed of the catheter pump and the peristaltic pump for the purge fluid. All controls and monitoring parameters for the system are displayed on a touch screen.

The speed of the DC motor, rotating wire and propeller is adjustable and is monitored and can be adjusted between 1,000 and 15,000 rpm.

The Purge System

The purge system is constructed to lubricate and to prevent entrance of blood into the rotating parts of the pump. The purge system consists of small channels inside the catheter to transport a 20% sterile glucose solution to lubricate the internal components. Heparin will be added to the purge fluid. ⅓ of the fluid is transported back through the inner lumen and lubricates the rotating wire. ⅔ of the glucose solution enters the circulation of the patient and seals off the shaft. The console controls the speed of the peristaltic pump.

In the following improvements of the catheter pump are explained.

The design mentioned above lacks a fixation mechanism to safely place and anchor the pump in the ascending aorta (above the aortic valve) when the pump is inserted into the patient from the groin.

The problems of the insertion via the femoral artery are:
1. The pump needs to cross the bow in the aortic arch.
2. The pump needs to be anchored in the ascending aorta in order to avoid movement against and touch the aortic valve.

However, the pump of today can be placed in the ascending aorta during heart surgery via a graft on the aortic arch or less commonly through the right (or left) carotid artery.

In the present patent application the pump head can be advanced further up in the aorta, crossing the aortic arch to be placed in the ascending aorta.

There are specific advantages by placing the catheter pump in the ascending aorta.

Backflow, the Aortic Valve and Coronary Perfusion

When the pump is placed in a tube (aorta), the rotation of the propeller will create a pressure gradient inside the tube, the upfront pressure being lower than the pressure behind the propeller. The pressure gradient creates a backward flow along the wall of the tube. Because the flow along the aortic wall occurs against the direction of the flow through the propeller it can be regarded as a loss of energy.

The aortic valve is tri-leaflet valve connected at the wall of the ascending aorta directly above the left ventricle. When the pump is placed above the aortic valve the backflow is stopped by the leaflets. The net effect is a higher pressure gradient.

In bench tests this pressure can increase to more than 3 times compared with the pressure obtained in a straight tube.

The impact of this is:
1. Reduced afterload of the left ventricle, which implies less work load on the left ventricle.
2. Because the coronary arteries exit above the leaflets the increased backward flow will increase the coronary perfusion pressure.
3. The placement of the pump before the exit of the cerebral arteries, will increase the perfusion of the brain.

The invention is also directed to a method to position the catheter pump according to the invention in the ascending aorta just above the aortic valve. Preferably the catheter is inserted via a puncture in the arterial system, preferably in the femoral artery in the groin preferably through an introducer sheath. The catheter pump then is brought and fixed in a position in the ascending aorta just above the aortic valve. In use, the catheter pump works in series with the heard.

The present invention will be described more in detail in the following with reference to the drawings in which.

Figure 1:
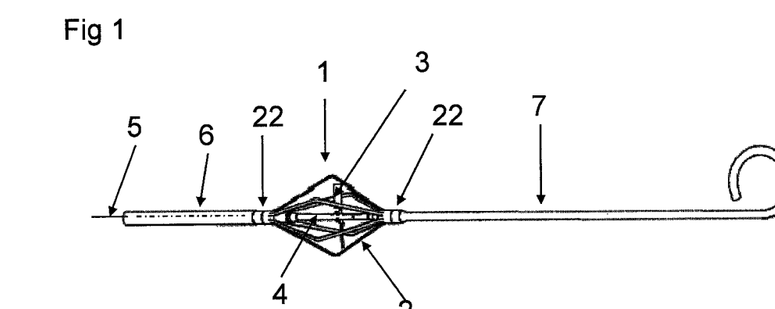
FIG. 1-3 show a first embodiment of the invention in which the pump head is anchored by means of an extension of the catheter, intended to be inserted into the heart.

FIG. 1 shows the distal end of a first embodiment of the catheter according the invention. 1 is the pumphead consisting of a cage 2 enclosing the propeller 3 on a drive shaft 4 connected to a drive cable 5 running through a sleeve 6. The pumphead 1 is shown in working position and provided with an extension 7 intended to be brought into the heart as shown in FIG. 3.

Figure 2:
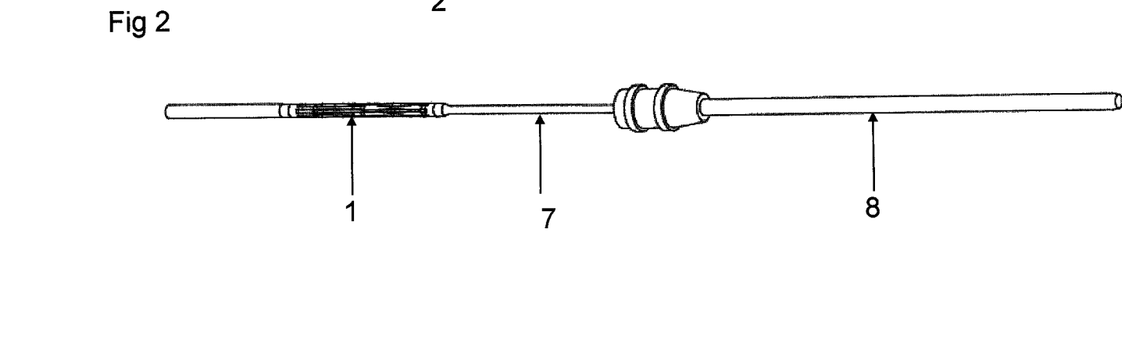

FIG. 2 shows the pumphead 1 in insertion position together with an introducer 8. The extension 7 is from its natural form shown in FIG. 1 stretched out and inserted partly into the introducer 8.

Figure 3:
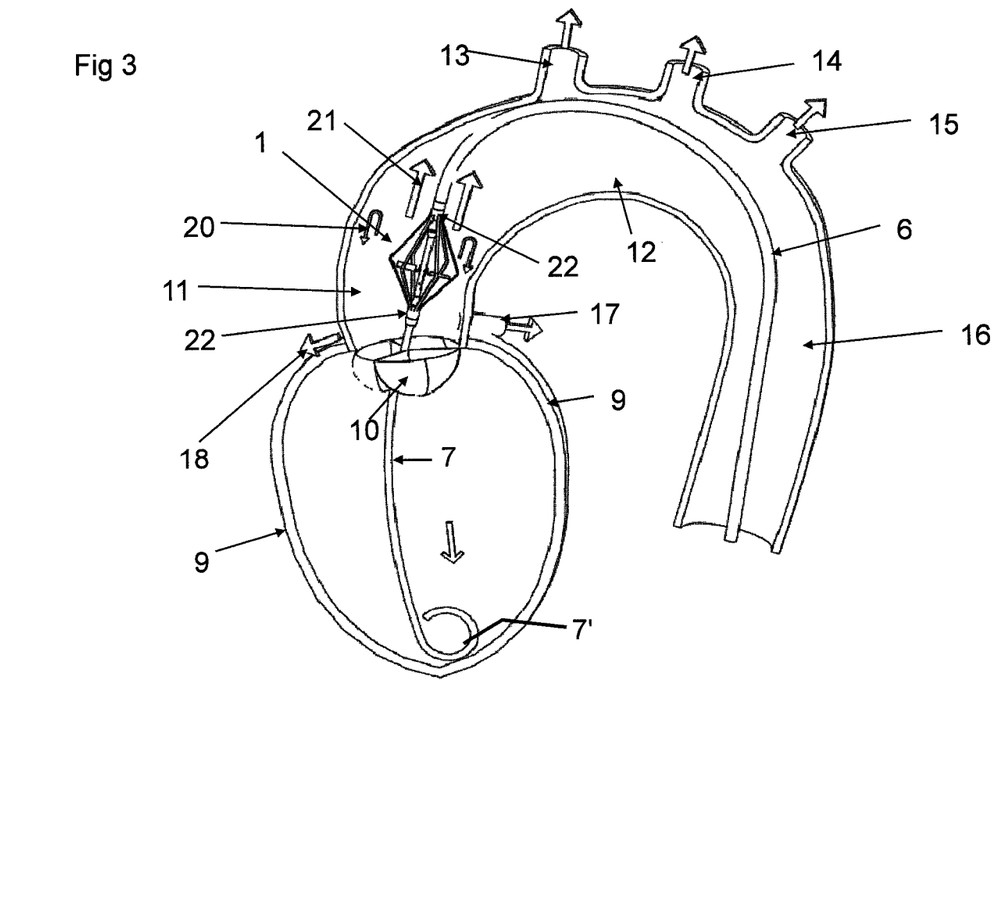

FIG. 3 shows the catheter in working position with its extension 7 inserted into the heart 9. The following details are important for the function of the pump:
10 the aortic valve
11 the ascending aorta 12 the aortic curve
13, 14 the carotid arteries
15 the subclavian artery
16 the descending aorta
17 the left coronary artery
18 the right coronary artery Details 20 and 21 will be described in the following.

As shown in FIG. 3, the extension 7 has a length in such a way, that if the distal end 7' of the extension 7 supports against the wall of the heart 9 the propeller 3 and the cage 2 are positioned outside the heart 9 but in the ascending aorta 11 near the aortic valve 10.

Figures 4, 5:
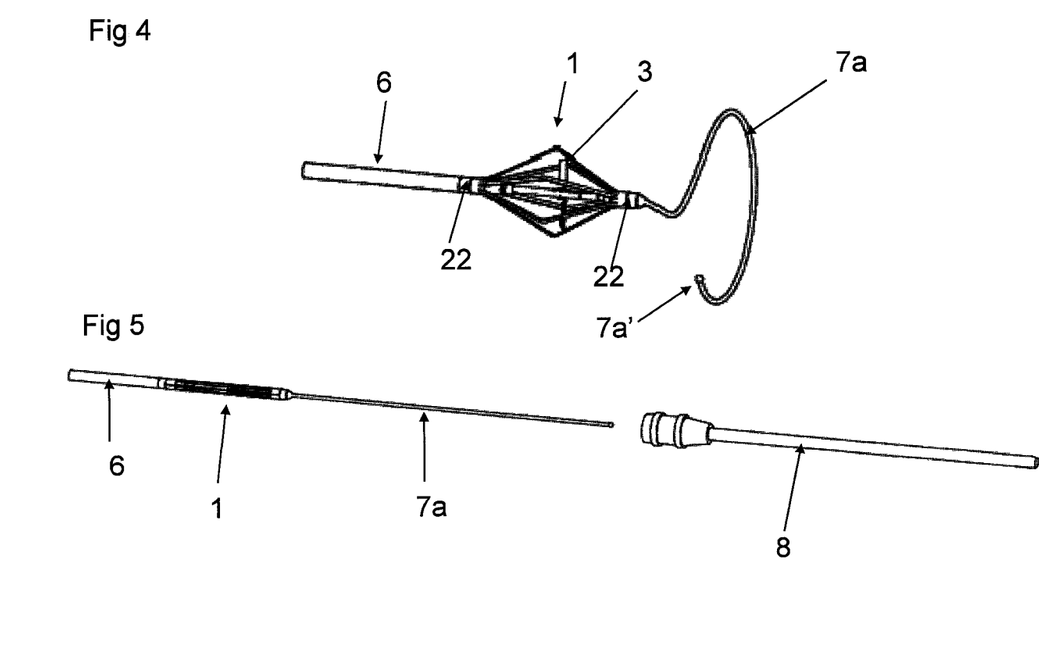
FIG. 4-6 show a second embodiment of the invention in which the pump head is anchored by means of an extension of the catheter, intended to rest around the outside of the aortic valve.
Figure 6:
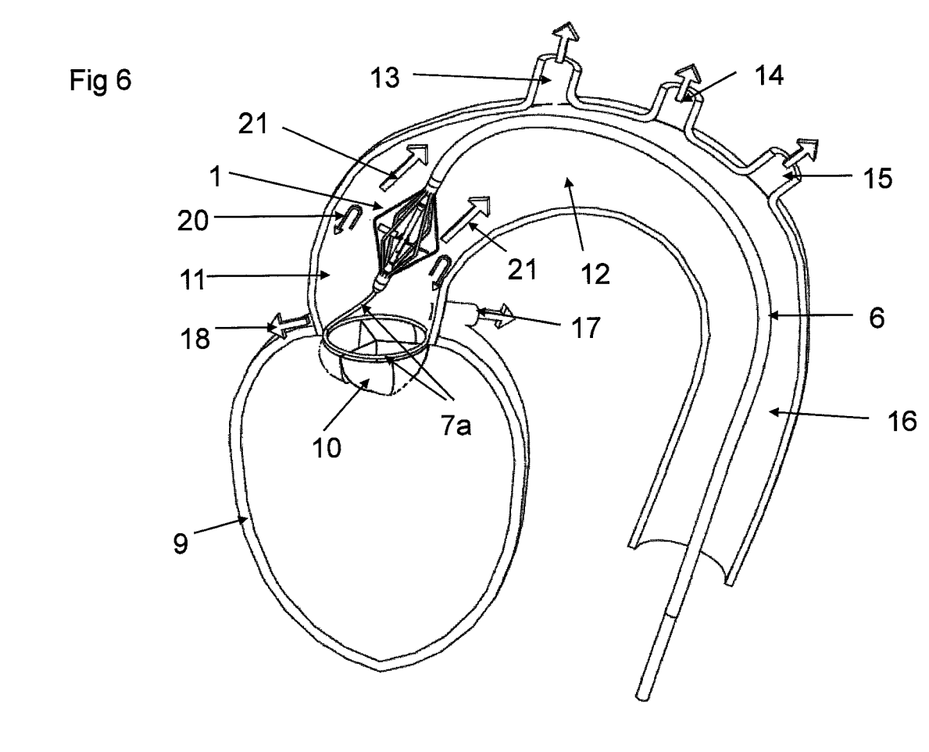

FIGS. 4, 5 and 6 show the distal end of a second embodiment of the catheter according to the invention in working position. The difference is that the extension 7a has the natural form of a circle or a section of a circle or a spiral but which can be inserted into the introducer 8 in a straight form as shown in FIG. 5. Inserted it will return to is natural form supporting the pumphead 1 resting around the outside of the aortic valve 10. As shown in FIGS. 5 and 6 the circle, section of a circle or spiral the extension 7a is located in a plane being perpendicular to the longitudinal axis of the catheter. Moreover, the extension 7a has at its distal end a distal tip 7a', being located in the anchored position direct at the proximal position of the aortic valve to enable a Device position in the ascending aorta 11.

Figure 7:
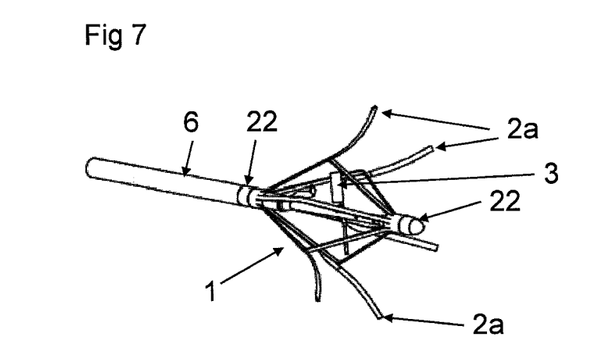
FIG. 7-9 show a third embodiment of the invention in which the pump head is anchored by means of parts of the cage surrounding the propeller, extending out from the cage and resting against the wall of the blood vessel.
Figure 8:
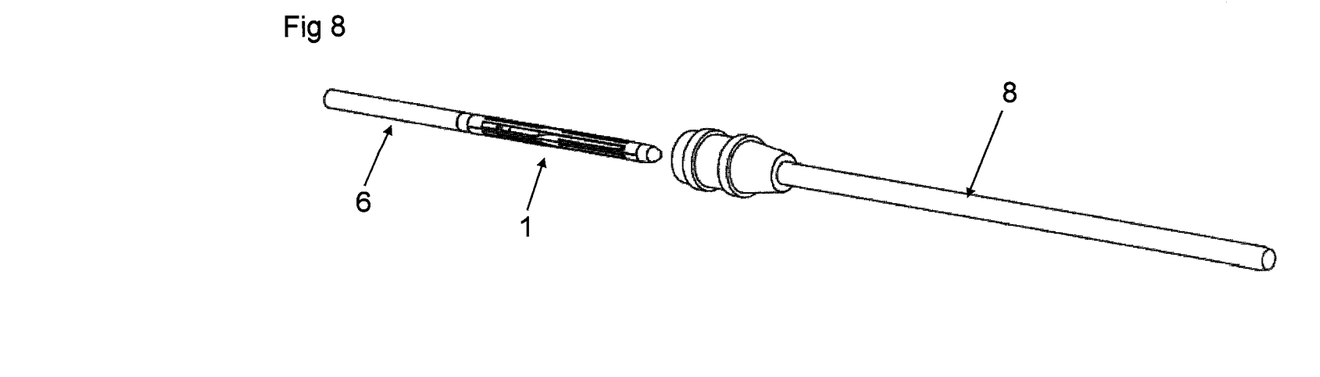
Figure 9:
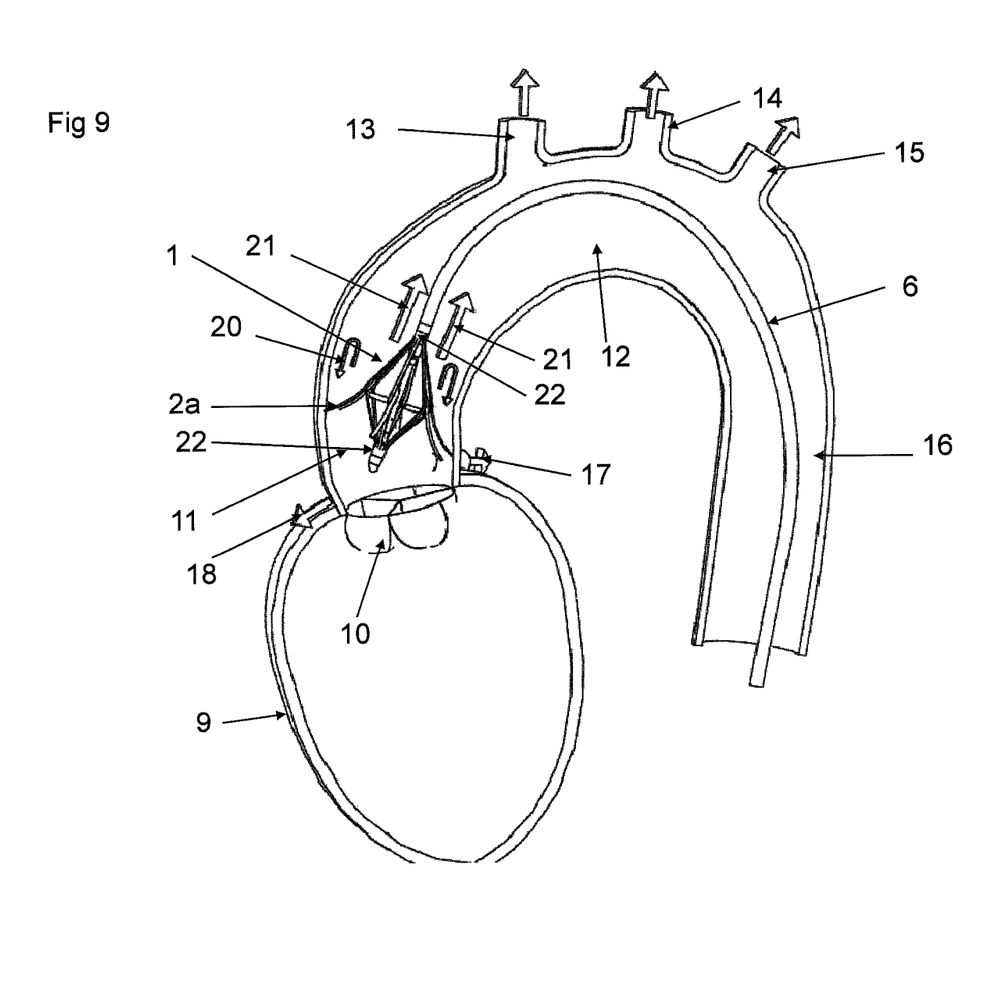

FIGS. 7, 8 and 9 show a third embodiment of the catheter according to the invention. The difference is that the cage 2 consisting of bands, threads or strips expandable from a position close to the drive shaft 4 to form the cage has some of bands, threads or strips or parts 2a of them arranged to extend out from the cage in order to contact the wall of the blood vessel and anchor the cage with the enclosed propeller in desired position.

A second embodiment based on the same principle is that the filaments are fixed on a ring at the tip of the pump head separate from the cage. The filaments are during insertion parallel and in parallel to the rotational axis of the pump head. They are constructed such that the natural form make them divert radially and fix against the wall of the vessel when deployed. The advantage is that the filaments are placed in a prolongation of the pump head to avoid an increased diameter of the cage.

Figures 10, 11:
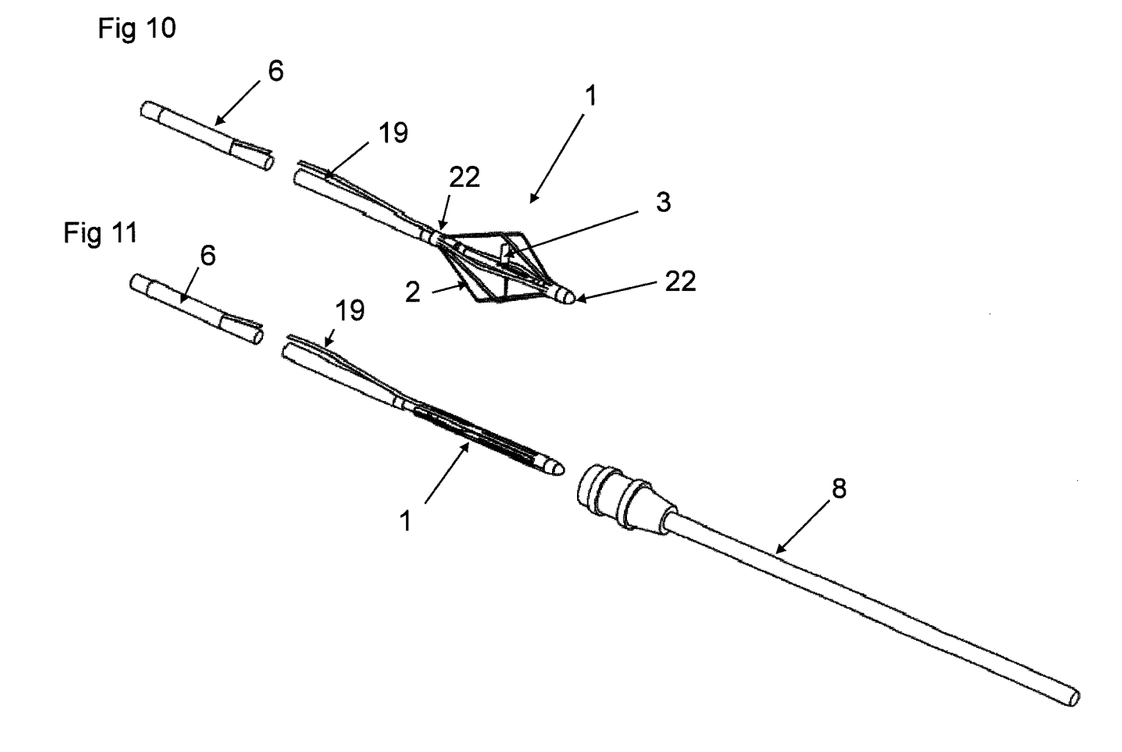
FIG. 10-12 show a fourth embodiment of the invention in which the pump is anchored by a together with the catheter insertable thread attached to the catheter near the drive rotor and which can be controlled from the outside.
Figure 12:
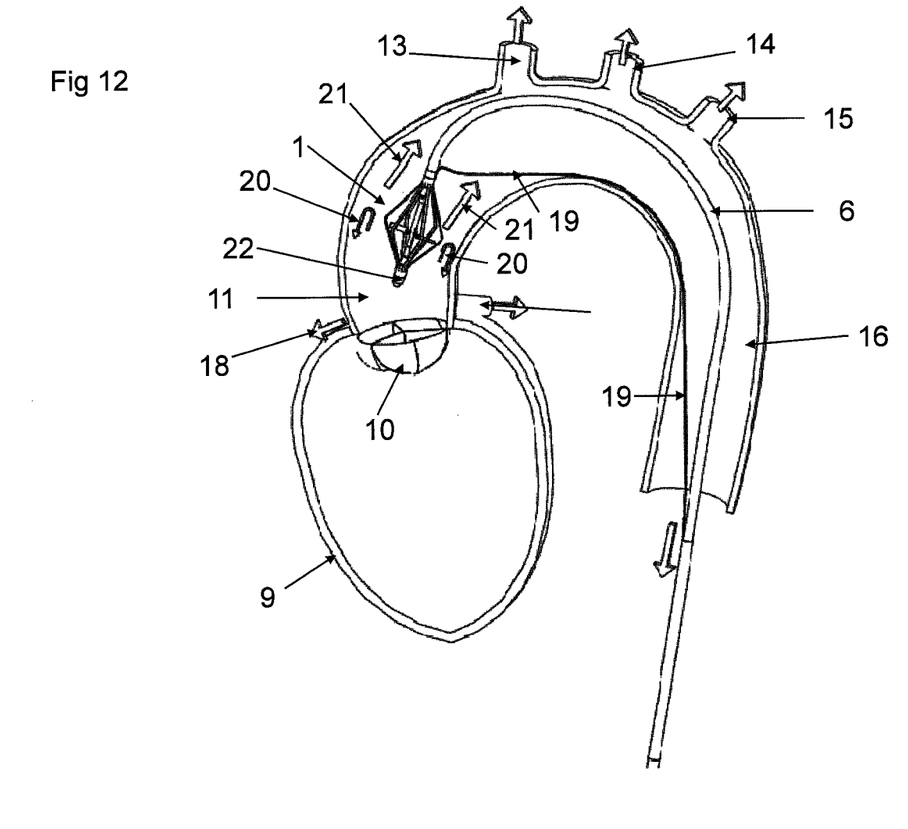

FIGS. 10, 11 and 12 show a fourth embodiment of the catheter according to the invention. The difference is that a thread 19 is attached near the pumphead 1 in order to be inserted together with the catheter. The thread 19 is controlled from the outside and can therefore be used to determine the position of the pumphead 1 in the ascending aorta 11.

By a position of the pumphead 1 in the ascending aorta 11 just above the aortic valve 10 a backflow is provided as shown by the arrows 20. Said backflow will increase the bloodflow to the left and right coronary arteries 17, 18. At the same time the ordinary pumpflow 21 increases the bloodflow to the carotid arteries 13, 14 and the subclavian artery 15.

Special advantages are gained when fixing the pumphead in the ascending aorta, but of course it could also be of advantage to fix the position when used in for instance the descending aorta.

The invention claimed is:

1. A catheter pump to be positioned in an ascending aorta of a human being, near an aortic valve, the catheter pump comprising:
   a catheter;
   an elongated sleeve;
   a propeller;
   a drive shaft;
   a drive cable extending through the elongated sleeve and connectable at a proximal end to an external drive source and connectable to the propeller near a distal end of the drive cable,
   wherein the propeller is mounted on the drive shaft and is connected with the drive cable;
   a cage including bands, threads or strips, whereby ends of a number of said bands, threads or strips are anchored in two sleeves, wherein the two sleeves are movable relative to each other along the drive shaft; and
   an extension of a distal end of the catheter, the extension comprising a straight portion and a bent distal end, the bent distal end is configured to be stretched out;
   wherein the propeller is enclosed in the cage, and the propeller and the cage are foldable from an insertion position close to the drive shaft to an expanded working position,
   wherein the drive shaft, the propeller, and the cage are located between the elongated sleeve and the extension, and
   wherein the extension is configured to be inserted into a heart and to be supported by the bent distal end against a wall of the heart, the straight portion having a length that when the bent distal end is supported against the wall of the heart, the propeller and the cage are positioned outside the heart but in the ascending aorta near the aortic valve.

2. The catheter pump of claim 1, wherein the cage has an open structure permitting backflow outside the propeller.

* * * * *

UNITED STATES PATENT AND TRADEMARK OFFICE
CERTIFICATE OF CORRECTION

| | | |
|---|---|---|
| PATENT NO. | : 8,617,239 B2 | Page 1 of 1 |
| APPLICATION NO. | : 13/320961 | |
| DATED | : December 31, 2013 | |
| INVENTOR(S) | : Oeyvind Reitan | |

It is certified that error appears in the above-identified patent and that said Letters Patent is hereby corrected as shown below:

On the title page item (73), replace the Assignee city "Chingen" with --Hechingen--

Signed and Sealed this
Seventeenth Day of June, 2014

Michelle K. Lee
*Deputy Director of the United States Patent and Trademark Office*